United States Patent [19]

Oxford et al.

[11] Patent Number: 4,918,080

[45] Date of Patent: Apr. 17, 1990

[54] IMIDAZOLLYL CONTAINING KETONE DERIVATIVES

[75] Inventors: Alexander W. Oxford, Royston; David J. Cavalla, London; Peter C. North, Royston, all of England

[73] Assignee: Glaxo Group Limited, London, England

[21] Appl. No.: 180,960

[22] Filed: Apr. 13, 1988

[30] Foreign Application Priority Data

Apr. 14, 1987 [GB] United Kingdom ............... 8708943
Jun. 5, 1987 [GB] United Kingdom ............... 8713227
Jun. 5, 1987 [GB] United Kingdom ............... 8713226
Jul. 15, 1987 [GB] United Kingdom ............... 8716698
Sep. 3, 1987 [GB] United Kingdom ............... 8720694

[51] Int. Cl.$^4$ ............... A61K 311/415; A61K 31/44; C07D 463/06; C07D 471/04
[52] U.S. Cl. ............... 514/300; 514/397; 546/113; 546/168; 548/336; 548/342; 540/524
[58] Field of Search ............... 546/113; 548/336; 514/300, 397; 540/524

[56] References Cited

U.S. PATENT DOCUMENTS

| | | | |
|---|---|---|---|
| 4,006,137 | 2/1977 | Haugwitz et al. | 548/336 |
| 4,808,581 | 2/1989 | Oxford et al. | 514/397 |

FOREIGN PATENT DOCUMENTS

| | | |
|---|---|---|
| 200444 | 11/1985 | European Pat. Off. |
| 191562 | 8/1986 | European Pat. Off. |
| 210840 | 2/1987 | European Pat. Off. |
| 219193 | 4/1987 | European Pat. Off. |
| 221702 | 5/1987 | European Pat. Off. |
| 315316 | 5/1989 | European Pat. Off. |
| 2153821A | 8/1985 | United Kingdom . |
| WO86/05783 | 10/1986 | World Int. Prop. O. . |

OTHER PUBLICATIONS

Fludzinski et al., "Indazoles as Indole Bioisosteres: Synthesis and Evaluation of the Tropanyl Ester and Amide of Indazole-3-carboxylate as Antagonists at the Serotonin 5HT$_3$ Receptor", *Journal of Medicinal Chemistry*, vol. 30, No. 9 (Sep., 1987).

Primary Examiner—Mary C. Lee
Assistant Examiner—Bernard I. Dentz
Attorney, Agent, or Firm—Bacon & Thomas

[57] ABSTRACT

The present invention provides ketones of the general formula (I):

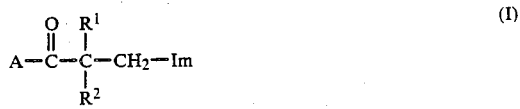

and physiologically acceptable salts and solvates thereof, wherein $R^1$ and $R^2$, which may be the same or different, each represents a hydrogen atom or a $C_{1-6}$alkyl group; Im represents an imidazolyl group of formula:

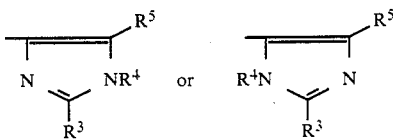

wherein one of the groups represented by $R^3$, $R^4$ and $R^5$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkyl group; and an aromatic or heteroaromatic group as defined in the specification.

The compounds are potent and selective antagonists of the effect of 5-HT at 5-HT$_3$ receptors and are useful, for example, in the treatment of psychotic disorders, anxiety and nausea and vomiting.

8 Claims, No Drawings

IMIDAZOLLYL CONTAINING KETONE DERIVATIVES

This invention relates to ketone derivatives, to processes for their preparation, to pharmaceutical compositions containing them and to their medical use. In particular the invention relates to compounds which act upon 5-hydroxytryptamine (5-HT) receptors of the type located on terminals of primary afferent nerves.

Compounds having antagonist activity at 'neuronal' 5-HT receptors of the type located on primary afferent nerves have been described previously.

Thus for example published U.K. patent specification No. 2,153,821A and published European patent specification Nos. 191,562, 219,193 and 210,840 disclose 3-imidazolylmethyltetrahydrocarbazolones which may be represented by the general formula:

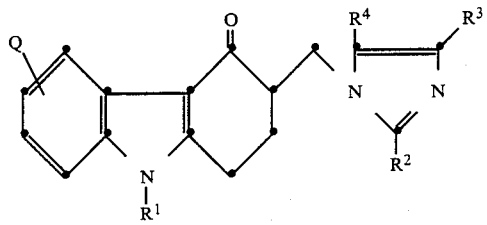

wherein $R^1$ represents a hydrogen atom or a group selected from $C_{1-10}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl or phenyl $C_{1-3}$ alkyl, and in the case where Q represents a hydrogen atom, $R^1$ may also represent $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl $C_{1-4}$ alkyl group, in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $-CO_2R^5$ or $-SO_2R^5$); one of the groups represented by $R^2$, $R^3$ and $R^4$ is a hydrogen atom or a $C_{1-6}$ alkyl, $C_{3-7}$ cycloalkyl, $C_{2-6}$ alkenyl, or phenyl $C_{1-3}$ alkyl group, and each of the other two groups, which may be the same or different, represents a hydrogen atom or a $C_{1-6}$ alkyl group; Q represents a hydrogen atom or a halogen atom or a hydroxy, $C_{1-4}$ alkoxy, phenyl $C_{1-3}$ alkoxy or $C_{1-6}$ alkyl group or a group $-NR^7R^8$ or $-CONR^7R^8$ (wherein $R^7$ and $R^8$, which may be the same or different, each represents a hydrogen atom or a $C_{1-4}$ alkyl or $C_{3-4}$ alkenyl group, or together with the nitrogen atom to which they are attached form a saturated 5 to 7 membered ring); and physiologically acceptable salts and solvates thereof.

In addition, published European patent specification No. 200,444 describes inter alia azabicyclo 3-indazole carboxylic acid ester and amide derivatives which may be represented by the general formula:

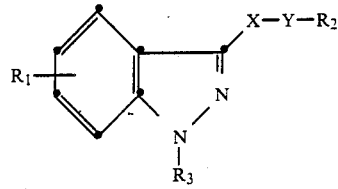

wherein
X represents CO and Y represents NH or O, or X represents NH and Y represents CO;

$R_1$ represents hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$-alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;

$R^3$ represents hydrogen, $C_{1-6}$ alkyl, $C_{3-7}$ alkenylmethyl, or phenyl or phenyl $C_{1-4}$ alkyl in which the phenyl group may optionally be substituted; and $R_2$ represents an azabicyclo group of the formula

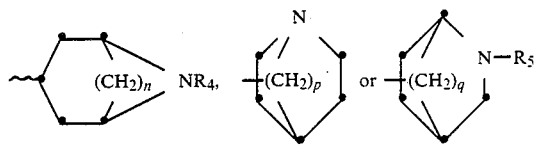

wherein n is 2 or 3; p and q are each independently 1 to 3; and $R_4$ or $R_5$ represents $C_{1-7}$ alkyl, $C_{3-8}$ cycloalkyl, $C_{3-8}$ cycloalkyl $C_{1-2}$ alkyl or $(CH_2)_tR_6$ (where t is 1 or 2, and $R_6$ is an optionally substituted thienyl, pyrrolyl, furyl or phenyl group).

We have now found a novel group of compounds which differ in structure from those described previously, and which are potent antagonists of the effect of 5-HT at 5-HT 'neuronal' receptors.

Thus, in one aspect the present invention provides a ketone of the general formula (I):

and physiologically acceptable salts and solvates thereof, wherein $R^1$ and $R^2$, which may be the same or different, each represents a hydrogen atom or a $C_{1-6}$ alkyl group; Im represents an imidazolyl group of formula:

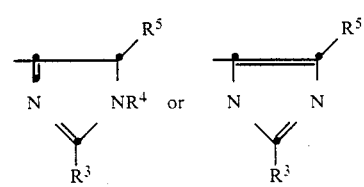

wherein one of the groups represented by $R^3$, $R^4$ and $R^5$ is a hydrogen atom or a $C_{1-6}$ alkyl, $C_{3-7}$ cycloalkyl, $C_{3-6}$ alkenyl, phenyl or phenyl $C_{1-3}$ alkyl group, and each of the other two groups, which may be the same or different, represents a hydrogen atom or a $C_{1-6}$ alkyl group; and A is a group of the formula (a), (b), (c), (d), (e), (f) or (g):

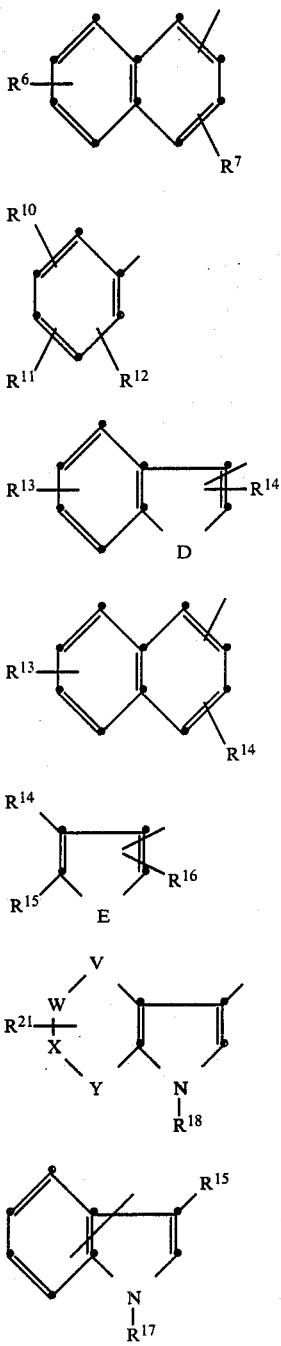

wherein $R^6$ and $R^7$, which may be the same or different, and may be attached to either the same or different fused rings of the naphthalene moiety, each represents a hydrogen atom, a halogen atom, or a hydroxy, $C_{1-4}$ alkoxy, $C_{1-4}$ alkyl or $C_{1-4}$ alkylthio group, and one of $R^6$ and $R^7$ may also represent a group —$NR^8R^9$ (wherein $R^8$ and $R^9$, which may be the same or different, each represents a hydrogen atom or a $C_{1-4}$ alkyl group, or together with the nitrogen atom to which they are attached form a saturated 5 to 7 membered ring);

$R^{10}$ represents a hydrogen atom, a halogen atom, or a hydroxy, $C_{1-4}$ alkoxy, $C_{1-4}$ alkyl, $C_{1-4}$ alkylthio, nitro or phenyl group, or a group —$NR^8R^9$ (wherein $R^8$ and $R^9$ are as defined previously);

$R^{11}$ represents a hydrogen atom, or a $C_{1-4}$ alkoxy or $C_{1-4}$ alkyl group;

$R^{12}$ represents a hydrogen atom, a halogen atom or a $C_{1-4}$ alkoxy group;

or, when $R^{10}$ represents a hydrogen atom, $R^{11}$ and $R^{12}$ may be attached to adjacent carbon atoms and form the group —$O(CH_2)_nO$— where n is 1 or 2;

$R^{13}$ represents a hydrogen atom, a halogen atom, or a hydroxy, $C_{1-4}$ alkoxy or $C_{1-4}$ alkyl group or a group —$NR^8R^9$ (wherein $R^8$ and $R^9$ are as defined previously);

$R^{14}$ represents a hydrogen atom, a halogen atom, or a $C_{1-4}$ alkyl or phenyl group;

D represents an oxygen atom or a sulphur atom;

$R^{15}$ represents a hydrogen atom, or a $C_{1-4}$ alkyl or phenyl group;

$R^{16}$ represents a hydrogen atom, a halogen atom or a $C_{1-4}$ alkyl group; with the provisos that when the group —$COCR^1R^2CH_2Im$ is attached at the 3-position of the group (e), $R^{14}$ represents a hydrogen atom, a halogen atom or a $C_{1-4}$ alkyl group, and $R^{16}$ represents a hydrogen atom or a $C_{1-4}$ alkyl group;

E represents an oxygen atom or a sulphur atom, or a group $NR^{17}$ wherein $R^{17}$ represents a hydrogen atom or a $C_{1-6}$ alkyl group;

$R^{18}$ represents a hydrogen atom or a group selected from $C_{1-6}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl, phenyl $C_{1-3}$ alkyl, —$CO_2R^{19}$, —$CONR^{19}R^{20}$ or —$SO_2R^{19}$ (wherein $R^{19}$ and $R^{20}$, which may be the same or different, each represents a hydrogen atom, a $C_{1-6}$ alkyl or $C_{3-7}$ cycloalkyl group, or a phenyl or phenyl $C_{1-4}$ alkyl group, in which the phenyl group is optionally substituted by one or more $C_{1-4}$ alkyl, $C_{1-4}$ alkoxy or hydroxy groups or halogen atoms, with the proviso that $R^{19}$ does not represent a hydrogen atom when $R^{18}$ represents a group —$CO_2R^{19}$ or —$SO_2R^{19}$);

$R^{21}$ represents a hydrogen atom or a halogen atom or a hydroxy, $C_{1-4}$ alkoxy, phenyl $C_{1-3}$ alkoxy or $C_{1-6}$ alkyl group or a group —$NR^{22}R^{23}$ or —$CONR^{22}R^{23}$ (wherein $R^{22}$ and $R^{23}$, which may be the same or different, each represents a hydrogen atom or a $C_{1-4}$ alkyl or $C_{3-4}$ alkenyl group, or together with the nitrogen atom to which they are attached form a saturated 5 to 7 membered ring);

V, W, X and Y each independently represent a nitrogen atom or the group —CH—, and Z represents a nitrogen atom or the group —$CR^{24}$ (where $R^{24}$ represents a hydrogen atom or a $C_{1-6}$ alkyl, $C_{3-6}$ alkenyl, $C_{3-7}$ cycloalkyl, phenyl or phenyl $C_{1-3}$ alkyl group), with the proviso that one and only one of V, W, X, Y and Z represents a nitrogen atom; and when A represents a group of formula (g), the group —$COCR^1R^2CH_2Im$ is attached at either the 2- or 4- position of the indole moiety.

In the group of formula (a), the substituent —$COCR^1R^2CH_2Im$ is attached at any available position of the naphthalene moiety. In the group of formula (c), one of the substituents $R^{14}$ and —$COCR^1R^2CH_2Im$ is at the 2-position and the other is at the 3-position of the benzofuran or benzothiophene moiety. In the group of formula (d), one of the substituents $R^{14}$ and —COCR$^1$R$^2$CH$_2$Im is at the 2, 3, or 4-position, and the other is at either of the two remaining available 2, 3 or 4-positions of the quinoline moiety. In the group of formula (e), one of the substituents $R^{16}$ and —COCR$^1$R$^2$CH$_2$Im is at the 2-position of the furan, thiophene or pyrrole ring, and the other is at the 3-position.

In the group of formula (b), the substituents $R^{10}$, $R^{11}$ and $R^{12}$ may be at any available position of the phenyl moiety. In the group of formula (c), the substituent $R^{13}$ may be at the 4, 5, 6 or 7-position of the benzofuran or benzothiophene moiety, and, in the group of formula (d), the substituent $R^{13}$ may be at the 5, 6, 7 or 8-position of the quinoline moiety. In the group of formula (f), the substituent $R^{21}$ may be attached to any available carbon atom of the six membered ring.

According to one aspect, the invention provides compounds of formula (I) wherein A represents a group (a) as defined in formula (I) ($R^1$, $R^2$ and Im being as defined in formula (I)).

According to another aspect, the invention provides compounds of formula (I) wherein A represents a group (b) as defined in formula (I) ($R^1$, $R^2$ and Im being as defined in formula (I)).

According to yet another aspect, the invention provides compounds of formula (I) wherein A represents a group (c) as defined in formula (I) ($R^1$, $R^2$ and Im being as defined in formula (I)).

According to a further aspect, the invention provides compounds of formula (I) wherein A represents a group (f) as defined in formula (I) ($R^1$, $R^2$ and Im being as defined in formula (I)).

According to a yet further aspect, the invention provides compounds of formula (I) wherein A represents a group (g) as defined in formula (I), wherein the group —COCR$^1$R$^2$Im is attached at the 2-position of the indole moiety ($R^1$, $R^2$ and Im being as defined in formula (I)).

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), a $C_{1-4}$ alkyl group (as such, or as part of a $C_{3-7}$ cycloalkyl $C_{1-4}$ alkyl group), may be a straight chain or branched chain alkyl group, for example, methyl, ethyl, propyl, prop-2-yl, butyl, but-2-yl or 2-methylprop-2-yl, and a $C_{1-6}$ alkyl group may also be, for example, a pentyl, pent-3-yl or hexyl group. An alkenyl group may be, for example, a propenyl or butenyl group. An alkynyl group may be, for example, a prop-2-ynyl or oct-2-ynyl group.

It is understood that when $R^4$ or $R^{18}$ represents a $C_{3-6}$ alkenyl group or $R^{18}$ represents a $C_{3-10}$ alkynyl group, or $R^{22}$ or $R^{23}$ represents a $C_{3-4}$ alkenyl group, the double or triple bond may not be adjacent to the nitrogen atom.

A phenyl $C_{1-3}$ alkyl group (as such or as part of a phenyl $C_{1-3}$ alkoxy group) may be, for example, a benzyl, phenethyl or 3-phenylpropyl group. A $C_{3-7}$ cycloalkyl group (as such or as part of a cycloalkylalkyl group) may be, for example, a cyclopropyl, cyclobutyl, cyclopentyl, cyclohexyl or cycloheptyl group. A $C_{1-4}$ alkoxy group may be, for example, a methoxy group. A halogen atom may be, for example, a fluorine, chlorine or bromine atom.

A preferred class of compounds of formula (I) is that in which $R^1$ and $R^2$ each represent a hydrogen atom.

Another preferred class of compounds of formula (I) is that in which $R^3$, $R^4$ and $R^5$ each independently represents a hydrogen atom or a $C_{1-4}$ alkyl (e.g. methyl) group. A further preferred class of compounds is that wherein $R^3$ and $R^4$ each represent a hydrogen atom, and $R^5$ is a $C_{1-6}$ alkyl, $C_{3-7}$ cycloalkyl, $C_{3-6}$ alkenyl, phenyl, or phenyl $C_{1-3}$ alkyl group, more particularly $C_{1-3}$ alkyl (e.g. methyl).

Another preferred class of compounds of formula (I) is that in which A is a group (a), and $R^6$ and $R^7$ each represent a hydrogen atom. A further preferred class of compounds of formula (I) in which A is a group (a) is that in which one of $R^6$ and $R^7$ represents a halogen atom (e.g. fluorine), or a hydroxy, $C_{1-4}$ alkoxy (e.g. methoxy) or $C_{1-4}$ alkyl (e.g. methyl) group, and the other is a hydrogen atom.

Another preferred class of compounds of formula (I) is that in which A is a group (b), and $R^{10}$ represents an amino group or, more preferably, a hydrogen atom or a $C_{1-4}$ alkyl (e.g. methyl), $C_{1-4}$ alkoxy (e.g. methoxy) or phenyl group, $R^{11}$ represents a $C_{1-4}$ alkoxy (e.g. methyl) group or, more preferably, a hydrogen atom or a $C_{1-4}$ alkyl (e.g. methyl) group, and $R^{12}$ represents a halogen atom (e.g. chlorine) or, more preferably, a hydrogen atom.

Another preferred class of compounds of formula (I) is that in which A is a group (c) or (d), and $R^{13}$ represents a hydrogen atom, and $R^{14}$ represents a hydrogen atom or a $C_{1-4}$ alkyl (e.g. methyl) group. When A is a group (d), the group —COCR$^1$R$^2$CH$_2$Im is preferably attached at the 4-position of the quinoline moiety.

Another preferred class of compounds of formula (I) is that in which A is a group (e), and two of $R^{14}$, $R^{15}$ and $R^{16}$ represent a $C_{1-4}$ alkyl (e.g. methyl) group, and the other represents a hydrogen atom. When E represents the group NR$^{17}$, $R^{17}$ is preferably a $C_{1-4}$ alkyl (e.g. methyl) group. A further preferred class of compounds of formula (I) in which A is a group (e) is that in which the group —COCR$^1$R$^2$CH$_2$Im is attached at the 3-position of the heterocycle.

Another preferred class of compounds of formula (I) is that in which A is a group (f), and one of Y and Z represents a nitrogen atom. When Y is a nitrogen atom, $R^{24}$ is preferably a hydrogen atom. A further preferred class of compounds of formula (I) in which A is a group (f) is that in which $R^{18}$ represents a hydrogen atom or, more preferably, a $C_{1-6}$ alkyl (e.g. methyl) group. A yet further preferred class of compounds of formula (I) in which A is a group (f) is that in which $R^{21}$ represents a hydrogen atom.

Another preferred class of compounds of formula (I) is that in which A is a group (g), and $R^{17}$ represents a $C_{1-4}$ alkyl (e.g. methyl) group. A further preferred class of compounds of formula (I) in which A is a group (g) is that in which $R^{15}$ represents a hydrogen atom.

Particularly preferred meanings of the group A are those represented by the formulae (a), (c) wherein the group —COCR$^1$R$^2$CH$_2$Im is attached at the 3-position of the benzofuran or benzothiophene moiety, (f), and (g)

wherein the group —COCR$^1$R$^2$CH$_2$Im is attached at the 4-position of the indole moiety.

Particularly preferred compounds according to the invention are:

3-(5-methyl-1H-imidazol-4-yl)-1-(1-naphthalenyl)-1-propanone;

1-(4-methoxy-1-naphthalenyl)-3-(5-methyl-1H-imidazol-4-yl)-1-propanone;

1-(2-hydroxy-1-naphthalenyl)-3-(5-methyl-1H-imidazol-4-yl)-1-propanone;

1-(benzo[b]thien-3-yl)-3-(5-methyl-1H-imidazol-4-yl)-1-propanone;

3-(5-methyl-1H-imidazol-4-yl)-1-(1-methyl-1H-indazol-3-yl)-1-propanone;

3-(5-methyl-1H-imidazol-4-yl)-1-(1-methyl-1H-indol-4-yl)-1-propanone; and their physiologically acceptable salts and solvates.

Compounds of the invention are potent and selective antagonists of 5-HT-induced responses of the rat isolated vagus nerve preparation and thus act as potent and selective antagonists of the 'neuronal' 5-HT receptor type located on primary afferent nerves. Receptors of this type are now designated as 5-HT$_3$ receptors. Such receptors are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting, particularly that associated with cancer chemotherapy and radiotherapy; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia and other cognitive disorders, which comprises administering an effective amount of a compound of formula (I) or a physiologically acceptable salt or solvate thereof.

Accordingly, the invention also provides a pharmaceutical composition which comprises at least one compound selected from ketone derivatives of the general formula (I), their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously, transcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine or 1-methyl-5-[[3-[3-(1-piperidinylmethyl)phenoxy]propyl]amino]-1H-1,2,4-triazole-3-methanol) or $H^+K^+$ATPase inhibitors (e.g. omeprazole).

A proposed dose of the compounds of the invention for administration to man (of approximately 70 kg body weight) is 0.001 to 100 mg, preferably 0.01 to 50 mg, most preferably 0.5 to 20 mg of the active ingredient per unit dose (expressed as the weight of free base) which could be administered, for example, 1 to 4 times per day. The dose will depend on the route of administration and the condition being treated. It will be appreciated that it may be necessary to make routine variations to the dosage depending on the age and weight of the patient as well as the severity of the condition to be treated.

According to another aspect of the invention, compounds of general formula (I) and physiologically acceptable salts or solvates thereof may be prepared by the general methods outlined hereinafter. In the following description, the groups A, $R^1$, $R^2$ and Im are as defined for compounds of general formula (I) unless otherwise stated.

According to a first general process (A) a compound of general formula (I), wherein $R^2$ represents a hydrogen atom, may be prepared by hydrogenation of a compound of formula (II):

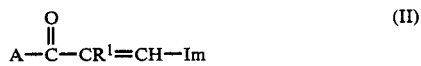

(II)

or a protected derivative thereof, followed where necessary by removal of any protecting groups.

Hydrogenation according to general process (A) may be effected using conventional procedures, for example using hydrogen in the presence of a noble metal catalyst (e.g. palladium, Raney nickel, platinum or rhodium). The catalyst may be supported on, for example, charcoal or alumina, or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), or an ester (e.g. ethyl acetate), or in a mixture of an alcohol and either a hydrocarbon (e.g. toluene) or a halogenated hydrocarbon (e.g. dichloromethane), and at a temperature in the range −20° to +100° C., preferably 0° to 50° C.

Compounds of formula (II) are novel compounds and constitute a further aspect of the invention. In addition, certain compounds of formula (II) are antagonists of the effect of 5-HT at 5-HT$_3$ receptors. A particular group of compounds of formula (II) is that in which A is a group (a) as defined in formula (I) ($R^1$ and Im being as defined in formula (I)). A preferred compound of formula (II) is (E)-3-(5-methyl-1H-imidazol-4-yl)-1-(1-naphthalenyl)-2-propen-1-one.

According to another general process (B), a compound of general formula (I) may be converted into another compound of formula (I) using conventional techniques. Such conventional techniques include hydrogenation, alkylation, acylation and acid-catalysed cleavage using protection and deprotection where necessary.

Thus, according to one embodiment of the interconversion process (B), hydrogenation may be used to convert an alkenyl or an alkynyl substituent into an alkyl substituent, or an alkynyl into an alkenyl substituent, or a benzyloxy substituent into a hydroxyl group. Hydrogenation according to general process (B) may be effected using conventional procedures, for example as described above for general process (A).

Alkylation according to process (B) may be used to effect C-, N- or O- alkylation at any appropriate position in the molecule, and the term 'alkylation' also includes the introduction of other groups such as cycloalkyl, alkenyl or phenalkyl groups.

Thus, for example, a compound of formula (I) in which one or both of $R^1$ and $R^2$ represents a $C_{1-6}$ alkyl group may be prepared by alkylating the corresponding compound of formula (I) in which one or both of $R^1$ and $R^2$ represent a hydrogen atom, or a compound in which one or both of $R^3$ and $R^4$ represent a $C_{1-6}$ alkyl, $C_{3-7}$ cycloalkyl, $C_{3-6}$ alkenyl or phenyl $C_{1-3}$ alkyl group may be prepared by alkylating the corresponding compound of formula (I) in which one or both of $R^3$ and $R^4$ represent a hydrogen atom.

The above alkylation reactions may be effected using the appropriate alkylating agent selected from compounds of formula $R^{25}L$ where $R^{25}$ represents a $C_{1-6}$ alkyl, $C_{3-7}$ cycloalkyl, $C_{3-6}$ alkenyl, $C_{3-10}$ alkynyl, $C_{3-7}$ cycloalkyl $C_{1-4}$ alkyl, or phenyl $C_{1-3}$ alkyl group, and L represents a leaving atom or group such as a halogen atom (e.g. chlorine, bromine or iodine), an acyloxy group (e.g. trifluoroacetyloxy or acetoxy), or a sulphonyloxy group (e.g. trifluoromethanesulphonyloxy, p-toluenesulphonyloxy or methanesulphonyloxy); or a sulphate of formula $(R^{25})_2SO_4$.

The alkylation reaction is conveniently carried out in an inert organic solvent such as a substituted amide (e.g. dimethylformamide), an ether (e.g. tetrahydrofuran) or an aromatic hydrocarbon (e.g. toluene), preferably in the presence of a base. Suitable bases include, for example, alkali metal hydrides (e.g. sodium hydride), alkali metal amides (e.g. sodium amide or lithium diisopropylamide), alkali metal carbonates (e.g. sodium carbonate) or an alkali metal alkoxide (e.g. sodium or potassium methoxide, ethoxide or t-butoxide). The reaction may conveniently be effected at a temperature in the range −80° to +100° C., preferably −80° to +50° C.

According to another embodiment of general process (B), a compound of formula (I) wherein $R^{18}$ represents $-CO_2R^{19}$, $-COR^{19}$, $-CONR^{19}R^{20}$ or $-SO_2R^{19}$ may be prepared by acylating or sulphonylating as appropriate, a compound of formula (I) wherein $R^{18}$ represents a hydrogen atom. The acylation/sulphonylation reactions may be effected using an appropriate acylating-/sulphonylating agent according to conventional procedures, for example, as described in published European patent specification No. 210,840.

According to a yet further embodiment of general process (B), a compound of formula (I) in which the group A contains a hydroxyl substituent may be prepared from the corresponding compound of formula (I) in which the group A is substituted by a $C_{1-4}$ alkoxy or benzyloxy group, by acid-catalysed cleavage. The reaction may be effected using a Lewis acid such as boron tribromide or aluminium trichloride, in a solvent such as a halogenated hydrocarbon (e.g. dichloromethane). The reaction temperature may conveniently be in the range $-80°$ to $+100°$ C.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect the imidazole nitrogen atom, or any of the indole or indazole nitrogen atoms that may be present, for example with an arylmethyl (e.g. benzyl or trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. It may also be necessary to protect any hydroxyl groups which may be present in the group A, for example with an arylmethyl (e.g. benzyl or trityl) group. When a hydroxy substituent in the group A is attached to the carbon atom adjacent to the position of attachment of the group $-COCR^1R^2CH_2Im$, this may be protected by cyclisation onto the $CH_2$ group of the $-COCR^1R^2CH_2Im$ moiety.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Green (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. An arylmethyl N-protecting group may be cleaved by hydrogenolysis in the presence of a catalyst (e.g. palladium on charcoal) and a trityl group may also be cleaved by acid hydrolysis (e.g. using dilute hydrochloric or acetic acid). An alkoxyalkyl group may be removed using a Lewis acid such as boron tribromide. An acyl group may be removed by hydrolysis under acidic or basic conditions (e.g. using hydrogen bromide or sodium hydroxide). A sulphonyl group may be removed by alkaline hydrolysis. An arylmethyl OH-protecting group may be cleaved under acidic conditions e.g. with dilute acetic acid, hydrobromic acid or boron tribromide) or by hydrogenolysis in the presence of a catalyst (e.g. palladium on charcoal). When a hydroxy substituent on the group A is protected by cyclisation onto the group $-COCR^1R^2CH_2Im$, deprotection may be effected by treatment with a base (e.g. potassium hydroxide).

A compound of formula (II) or a protected derivative thereof, may be prepared by condensing a compound of formula (III):

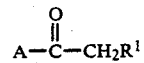
(III)

or a protected derivative thereof, with a compound of formula (IV):

(IV)

or a protected derivative thereof, in the presence of a base such as an alkali metal hydroxide or alkoxide, followed where necessary by removal of any protecting groups.

The reaction may conveniently be effected using an alkali metal hydroxide (e.g. sodium or potassium hydroxide) in an alcohol (e.g. methanol or ethanol) or water, or mixtures thereof, or using an alkali metal alkoxide (e.g. sodium ethoxide or potassium t-butoxide) in the corresponding alcohol (e.g. ethanol or t-butanol) or in an inert solvent such as an ether (e.g. tetrahydrofuran), at a temperature in the range of 0° to 100° C.

Alternatively, the condensation between compounds of formulae (III) and (IV) or protected derivatives thereof may be carried out in the presence of a base such as an alkali metal amide (e.g. lithium diisopropylamide) in an inert solvent such as an ether (e.g. tetrahydrofuran), followed by dehydration, and removal of any protecting groups where necessary.

The dehydration process may be effected using conventional methods, for example by using an organic or mineral acid (e.g. p-toluenesulphonic or hydrochloric acid) in a suitable solvent such as an ether (e.g. tetrahydrofuran), an alcohol (e.g. methanol), or glacial acetic acid, at a temperature in the range of 0° to 100° C.

Compounds of formula (III) are either known or may be prepared from known compounds by conventional methods, such as, for example, treating the corresponding carboxylic acid with an appropriate alkyllithium reagent $R^1CH_2Li$.

Compounds of formula (IV) may be prepared as described in published European patent specification No. 242,973.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The various general methods described above may be used for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in 0° C. Thin layer chromatography (t.l.c.) was carried out on silica, and flash column chromatography (FCC) and short-path column chromatography (SPCC) on silica (Merck 9385 and 7747 respectively). Solvent System A as used for chromatography denotes dichloromethane:ethanol:0.88 ammonia solution and System B denotes ethyl acetate:hexane. Organic extracts were dried over sodium sulphate or magnesium sulphate. The following abbreviations are used: THF-tetrahydrofuran, DMF-dimethylformamide.

Intermediate 1 is
5-methyl-1-(triphenylmethyl)-1H-imidazole-4-carboxaldehyde.

Intermediate 2

1-(5-Fluoro-1-naphthalenyl)ethanone

Methyl lithium (1.4M solution in ether; 6.6 ml) was added dropwise to a stirred solution of 5-fluoro-1-naphthalene carboxylic acid (870 mg) in dry THF (15 ml) at −78° under nitrogen. The reaction mixture was allowed to warm to room temperature over 2 h and was treated with 2N sodium hydroxide (60 ml). The mixture was extracted with ether (2×30 ml), and the combined, dried organic extracts were evaporated to give the *title compound* (865 mg) as an oil, t.l.c. (System B, 1:6) Rf 0.3.

Intermediate 3

1-(1,2,4-Trimethyl-1H-pyrrol-3-yl)ethanone

A solution of 3-acetyl-2,4-dimethylpyrrole (2.0 g) in dry DMF (30 ml) was added dropwise, with stirring, to a suspension of sodium hydride (78% dispersion in oil; 565 mg) in dry DMF (15 ml) at 0° under nitrogen and stirring was continued at room temperature for 1 h. Iodomethane (1.14 ml) was added dropwise at 0° and stirring was continued for 1.5 h. The suspension was evaporated, treated with 8% aqueous sodium bicarbonate (80 ml) and extracted with ethyl acetate (2×80 ml). The combined, dried organic extracts were evaporated to give a solid (2.1 g) which was dissolved in dichloromethane (20 ml) and adsorbed onto silica gel (Merck 7734, 6 g). This was applied to an FCC column and elution with System B (1:3) afforded the *title compound* (1.89 g) as crystals, m.p. 68°–70°.

Intermediate 4

1-(1-Methyl-1H-indazol-3-yl)ethanone

Methyl lithium (1.58M solution in ether; 13.8 ml) was added dropwise to a stirred, cold (−60°) solution of 1-methyl-1H-indazole-3-carboxylic acid (1.77 g) in dry THF (60 ml) under nitrogen and stirring was continued while warming to 0° over 2 h. The reaction mixture was quenched with saturated ammonium chloride solution (50 ml), and the layers were separated. The aqueous layer was further extracted with dichloromethane (2×50 ml) and the combined organic layers were washed with brine (2×50 ml), dried and evaporated in vacuo. The residual solid (1.8 g) was purified by FCC eluting with System B (1:4) to give the *title compound* (1.3 g), m.p. 86°–88°.

Intermediate 5

1-(6-Fluoro-1-naphthalenyl)ethanone

Methyl lithium (1.59M solution in ether; 4.2 ml) was added dropwise to a stirred solution of 6-fluoro-1-naphthalene carboxylic acid (640 mg) in dry THF (10 ml) at −78° under nitrogen. The solution was stirred at −78° for 2 h and was slowly allowed to warm to −15°. The solution was quenched with saturated aqueous ammonium chloride (1 ml) and partitioned between 2N sodium hydroxide (25 ml) and ethyl acetate (25 ml). The organic phase was dried and evaporated to give the *title compound* (404 mg) as an oil, t.l.c. (System B, 1:6) Rf 0.2.

Intermediate 6

(E)-3-[5-Methyl-1-(triphenylmethyl)-1H-imidazol-4-yl]-1-(2-naphthalenyl)-2-propen-1-one A solution of 2-acetylnaphthalene (0.965 g) and Intermediate 1 (2.0 g) in ethanol (40 ml) was treated with a solution of potassium hydroxide (2.5 g) in water (15 ml), and the mixture was stirred overnight. The resulting precipitate was filtered off, recrystallised from ethanol/water (6:1; 50 ml) and dried (in vacuo, 95°, 2 h) to give the *title compound* (1.90 g), m.p. 197°–199°. Concentration of the mother liquors in vacuo followed by dilution with water afforded a second crop of the title compound (0.59 g), m.p. 194°–197°.

Intermediate 7

(E)-3-[5-Methyl-1-(triphenylmethyl)-1H-imidazol-4-yl]-1-phenyl-2-propen-1-one

A solution of acetophenone (681 mg) and Intermediate 1 (2.0 g) in ethanol (40 ml) was treated with a solution of potassium hydroxide (2.48 g) in water (15 ml), and the mixture was stirred overnight. The resulting precipitate was filtered off, recrystallised from ethanol/water (4:1; 50 ml) and dried (in vacuo, 95°, 2 h) to give the *title compound* (2.30 g) as crystals, m.p. 209°–211°.

Intermediate 8

(E)-3-[5-Methyl-1-(triphenylmethyl)-1H-imidazol-4-yl]-1-(1-naphthalenyl)-2-propen-1-one A solution of 1-acetylnaphthalene (0.965 g) and Intermediate 1 (2.0 g) in ethanol (40 ml) was treated with a solution of potassium hydroxide (2.5 g) in water (15 ml), and was stirred for 36 h at room temperature. The mixture was filtered and the solid was recrystallised twice from ethanol (30 ml) to give the *title compound* (1.17 g) as needles, m.p. 184°–186°. The mother liquors were combined and evaporated in vacuo to leave a solid (ca. 1.6 g) which was purified by SPCC eluting with System B (3:7) to give a second crop of the *title compound* (0.58 g), m.p. 184°–186°.

Intermediate 9

(E)-3-[5-Methyl-1-(triphenylmethyl)-1H-imidazol-4-yl]-1-(4-quinolinyl)-2-propen-1-one Potassium hydroxide (1.8 g) in water (5 ml) was added to a stirred suspension of 4-acetylquinoline (700 mg) and Intermediate 1 (1.44 g) in absolute ethanol (30 ml). After 2 h the reaction mixture was partitioned between water (150 ml) and dichloromethane (3×150 ml) and the combined, dried organic layers were evaporated in vacuo to leave a foam (2.2 g) which was purified by FCC eluting with ether→dichloromethane/ethanol (95:5) to give the *title compound* (550 mg), t.l.c. (ether) Rf 0.11.

Intermediate 10

(E)-3-(5-Methyl-1H-imidazol-4-yl)-1-(1-naphthalenyl)-2-propen-1-one maleate

A solution of (E)-3-[5-methyl-1-(triphenylmethyl)-1H-imidazol-4-yl]-(1-naphthalenyl)-2-propen-1-one (1.0 g) in a mixture of water (10 ml), THF (10 ml) and acetic acid (10 ml) was heated at reflux under nitrogen for 1 h. The cooled reaction mixture was partitioned between ethyl acetate (100 ml; discarded) and 0.4N hydrochloric acid (2×75 ml). The combined acidic layers were basified with potassium carbonate (to pH8) and extracted with dichloromethane (3×50 ml). The combined dichloromethane extracts were dried and evaporated in vacuo to give the free base of the title compound (0.51 g) as a solid. This was dissolved in hot methanol (15 ml), and a solution of maleic acid (0.23 g) in methanol (2 ml) was added with stirring. Cooling precipitated the *title compound* (0.62 g), m.p. 170°–173° (decomp.).

Analysis Found: C,67.0; H,4.8; N,7.4; $C_{17}H_{14}N_2O \cdot C_4H_4O_4$ requires C,66.7; H,4.8; N,7.4%.

Intermediates 11, 12 and 13 were all prepared in a similar manner to Intermediate 10 by deprotection of the appropriate tritylated enone, followed by salt formation.

Intermediate 11

(E)-3-(5-Methyl-1H-imidazol-4-yl)-1-(2-naphthalenyl)-2-propen-1-one maleate

The deprotection of (E)-3-[5-methyl-1-(triphenylmethyl)-1H-imidazol-4-yl]-1-(2-naphthalenyl)-2-propen-1-one (1.25 g) followed by maleate formation gave the *title compound* (0.75 g), m.p. 190°–191° (decomp.).

Intermediate 12

(E)-3-(5-Methyl-1H-imidazol-4-yl)-1-phenyl-2-propen-1-one maleate

The deprotection of (E)-3-[5-methyl-1-(triphenylmethyl)-1H-imidazol-4-yl]-1-phenyl-2-propen-1-one (1.25 g) gave a solid which was triturated with ether (50 ml) to give the free base of the title compound (0.40 g). This was dissolved in methanol (20 ml), and a solution of maleic acid (0.23 g) in ethanol (2 ml) was added with stirring. After dilution with ethyl acetate (10 ml) the mixture was filtered to give the *title compound* (0.56 g) as a crystalline solid, m.p. 178°–179°.

Intermediate 13

3-(5-Methyl-1H-imidazol-4-yl)-1-(4-quinolinyl)-2-propen-1-one succinate

The deprotection of (E)-3-[5-methyl-1-(triphenylmethyl)-1H-imidazol-4-yl]-1-(4-quinolinyl)-2-propen-1-one (550 mg) gave the free base of the title compound (275 mg) which was dissolved in absolute ethanol (3 ml) and a solution of succinic acid (127 mg) in methanol (1 ml) was added. Concentration of the solution to ca. 0.5 ml and dilution with dry ether afforded the *title compound* (225 mg) as a solid, m.p. 154°–156°.

Intermediate 14

1-(5-Fluoro-1-naphthalenyl)-3-(5-methyl-1H-imidazol-4-yl)-2-propen-1-one

A solution of potassium hydroxide (390 mg) in methanol (5 ml) was added to a suspension of 1-(5-fluoro-1-naphthalenyl)ethanone (830 mg) and Intermediate 1 (1.55 g) in methanol (20 ml) and the mixture was heated at reflux for 4 h. The solution was treated with THF (25 ml), water (25 ml) and acetic acid (10 ml) and was then heated at reflux for a further 2 h. The solution was added cautiously to 8% aqueous sodium bicarbonate (170 ml) and was extracted with dichloromethane (2×50 ml). The extracts were dried and evaporated to give an oil which was purified by FCC eluting with System A (100:3:0.3)→(100:10:1) to give the *title compound* (1.06 g) as a foam, t.l.c. (System A, 100:10:1) Rf 0.4.

Intermediate 15

(E)-1-(2-Methoxyphenyl)-3-(5-methyl-1H-imidazol-4-yl)-2-propen-1-one

A mixture of 2'-methoxyacetophenone (0.85 g), Intermediate 1 (2.0 g) and potassium hydroxide (0.5 g) in methanol (25 ml) was stirred at 23° for ca. 70 h. The mixture was diluted with acetic acid (20 ml), water (20 ml) and ethanol (80 ml) and heated on a steam bath for 2 h. The resulting mixture was partitioned between 1M hydrochloric acid (3×75 ml) and ethyl acetate (200 ml; discarded). The aqueous layer was basified with potassium carbonate (to pH9) and extracted with ethyl acetate (3×200 ml). The combined, dried organic extracts were evaporated to leave a gum (ca. 1.2 g) which was purified by SPCC eluting with System A (200:8:1) to give the *title compound* (0.48 g) as a foam, t.l.c. (System A, 100:8:1) Rf 0.41.

Intermediate 16

(E)-3-(5-Methyl-1H-imidazol-4-yl)-1-(3,5-dimethylphenyl)-2-propen-1-one

A mixture of 3,5-dimethylacetophenone (0.5 g) and Intermediate 1 (1.2 g) (0.3 g) in methanol (5 ml), and the mixture was kept at 23° for 3 days. The mixture, from which some crystals had separated, was then stirred with cooling (0°) for 15 min, filtered and the resultant solid was washed with cold methanol and dried. This solid (1.1 g) was heated at reflux in a mixture of THF (20 ml), acetic acid (5 ml) and water (5 ml) for 1 h. The mixture was concentrated in vacuo to ca. 10 ml, diluted with ethyl acetate (50 ml) and washed with 2N aqueous sodium carbonate (2×50 ml; discarded). The organic phase was evaporated to give a solid which was purified by FCC eluting with ethyl acetate/methanol/triethylamine (90:10:1) to give the *title compound* (0.32 g), m.p. 165°–166°.

Intermediate 17

(E)-1-(2-Methyl-3-benzofuranyl)-3-(5-methyl-1H-imidazol-4-yl)-2-propen-1-one

A solution of potassium hydroxide (0.5 g) in methanol (5 ml) was added to a solution of Intermediate 1 (2.0 g) and 3-acetyl-2-methylbenzofuran (1.0 g) in methanol (25 ml), and the mixture was stirred at room temperature for 5 days. The resultant solid (1.11 g) was filtered off and heated at reflux in a mixture of acetic acid (30 ml), water (30 ml) and THF (30 ml) for 1.5 h. The reaction mixture was poured into 1N hydrochloric acid (120 ml) and washed with ethyl acetate (120 ml). The aqueous layer was basified with potassium carbonate (to pH9), extracted with dichloromethane (3×120 ml) and the combined extracts were dried and evaporated to give an oil (0.30 g). The ethyl acetate wash was evaporated to give a solid (ca. 0.90 g) and the two batches were combined and triturated with ethyl acetate/methanol (19:1) to give the *title compound* (0.34 g) as a solid, m.p. 166°–168°.

Intermediate 18

(E)-1-(2-Methylbenzo[b]thien-3-yl)-3-(5-methyl-1H-imidazol-4-yl)-2-propen-1-one

A solution of potassium hydroxide (200 mg) in methanol (2 ml) was added to a solution of Intermediate 1 (741 mg) and 3-acetyl-2-methylbenzo[b]thiophene (400 mg) in methanol (10 ml), and the mixture was stirred at room temperature for 16 h. The resultant solid (780 mg) was filtered off and heated at reflux in a mixture of acetic acid (20 ml), water (20 ml) and THF (20 ml) for 1.5 h. The THF was removed in vacuo, 1N hydrochloric acid (80 ml) was added and the solution was washed with ethyl acetate (80 ml; discarded). The aqueous layer was basified with potassium carbonate (to pH9) and extracted with dichloromethane (3×80 ml). The combined organic extracts were dried and evaporated to give the *title compound* (217 mg) as a solid, m.p. 154°–156°.

Intermediate 19

(E)-1-(3-Benzofuranyl)-3-(5-methyl-1H-imidazol-4-yl)-2-propen-1-one

A mixture of 3-acetylbenzofuran (0.91 g), Intermediate 1 (2.0 g) and potassium hydroxide (0.50 g) in methanol (15 ml) was stirred at room temperature under nitrogen for 4 days. The resultant solid was then treated according to the method of Intermediate 18 to give a solid which was purified by FCC eluting with System A (100:10:1) to give the *title compound* (0.32 g), m.p. 192°–193°.

Intermediate 20

(E)-1-[Benzo[b]thien-2-yl]-3-(5-methyl-1H-imidazol-4-yl)-2-propen-1-one

A solution of potassium hydroxide (0.5 g) in methanol (5 ml) was added to a suspension of 2-acetylbenzo[b]thiophene (1.0 g) and Intermediate 1 (2.0 g) in methanol (25 ml), and the mixture was stirred at room temperature for 19 h. The suspension was filtered and the collected solid was dried in vacuo. The resultant solid (2.33 g) was heated at reflux in a mixture of acetic acid (8 ml), water (5 ml) and THF (25 ml) for 3 h. The reaction mixture was added cautiously to 8% aqueous sodium bicarbonate (200 ml) and extracted with dichloromethane (3×60 ml). The combined organic extracts were dried and evaporated to give a solid which was purified by FCC eluting with System A (100:8:0.8) to give the *title compound* as a solid (0.76 g), m.p. 188°–190°.

Intermediate 21

(E)-1-(2-Benzofuranyl)-3-(5-methyl-1H-imidazol-4-yl)-2-propen-1-one

A mixture of 2-acetylbenzofuran (0.91 g), Intermediate 1 (2.0 g) and potassium hydroxide (0.50 g) in methanol (15 ml) was stirred at room temperature under nitrogen for 24 h. The suspension was evaporated, treated with water (50 ml) and extracted with dichloromethane (50 ml). The organic extract was dried and evaporated, and the resultant oil was heated at reflux in a mixture of acetic acid/water/THF (1:1:1; 50 ml) for 1 h. The cooled reaction mixture was evaporated and the resultant solid was treated with 1N hydrochloric acid (70 ml) and extracted with ethyl acetate (60 ml; discarded). The aqueous phase was basified with 2N sodium carbonate (75 ml) and extracted with dichloromethane (2×100 ml). The combined, dried organic extracts were evaporated to give a foam (ca. 1.6 g) which was purified by SPCC eluting with System A (945:50:5) to give the *title compound* (0.82 g) as a foam, t.l.c. (System A, 945:50:5) Rf 0.12.

Intermediate 22

(E)-3-(5-Methyl-1H-imidazol-4-yl)-1-(1-methyl-1H-indol-2-yl)-2-propen-1-one

A mixture of 1-(1-methyl-1H-indol-2-yl)ethanone (250 mg), Intermediate 1 (520 mg) and potassium hydroxide (130 mg) in methanol (7 ml) was heated at 50° for 20 h under nitrogen. The reaction mixture was treated according to the method of Intermediate 21 to give a solid which was purified by FCC eluting with System A (912:80:8) to give the *title compound* (337 mg) as crystals, m.p. 222°–224°.

Intermediate 23

(E)-3-(5-Methyl-1H-imidazol-4-yl)-1-(1,2,4-trimethyl-1H-pyrrol-3-yl)-2-propen-1-one A solution of potassium hydroxide (250 mg) in methanol (3 ml) was added to a suspension of Intermediate 1 (1.0 g) and 3-acetyl-1,2,4-trimethyl-1H-pyrrole (430 mg) in methanol (12 ml), and the suspension was stirred at reflux under nitrogen for 65 h. The reaction mixture was treated according to the method of Intermediate 21 to give a foam (670 mg) which was purified by FCC eluting with System A (89:10:1) to give the *title compound* (580 mg) as a powder, t.l.c. (System A, 89:10:1) Rf 0.28.

Intermediate 24

(E)-1-(2,5-Dimethyl-3-furanyl)-3-(5-methyl-1H-imidazol-4-yl)-2-propen-1-one

A solution of potassium hydroxide (650 mg) in methanol (7 ml) was added to a suspension of Intermediate 1 (2.60 g) and 3-acetyl-2,5-dimethylfuran (1.0 g) in methanol (30 ml), and the suspension was stirred at room temperature for 5 days. The reaction mixture was treated according to the method of Intermediate 21 to give a solid (1.0 g). This was dissolved in ethanol (50 ml) and adsorbed onto silica gel (Merck 7734, 3 g) which was then applied to an SPCC column. Elution with System A (189:10:1) gave the *title compound* as an oil (710 mg), t.l.c. (System A, 189:10:1) Rf 0.15.

Intermediate 25

(E)-1-(2,5-Dimethyl-3-thienyl)-3-[5-methyl-1H-imidazol-4-yl]-2-propen-1-one hemi-succinate A mixture of 3-acetyl-2,5-dimethylthiophene (0.43 ml) and Intermediate 1 (1.06 g) in ethanol (60 ml) was treated with a solution of potassium hydroxide (0.8 g) in water (2 ml). The resulting solution was stirred at 20° for 21 h and heated on a steam bath for 2 h. The mixture was then cooled to 20°, treated with glacial acetic acid (15 ml) and heated on a steam bath for 2 h. The acidic reaction mixture was cooled (20°) and partitioned between saturated potassium carbonate solution (250 ml) and ethyl acetate (2×250 ml). The combined, dried organic extracts were evaporated to give a gum (ca. 2 g) which was purified by FCC eluting with System A (100:8:1) to give a solid (0.55 g). This was dissolved in absolute ethanol (30 ml) and treated with a solution of succinic acid (0.264 g) in ethanol (30 ml). The resulting solution was concentrated in vacuo to ca. 5 ml and diluted with dry ether (50 ml) to precipitate the *title compound* (0.57 g), m.p. 163°–165°.

Intermediate 26

(E)-1-(4-Methoxy-1-naphthalenyl)-3-[5-methyl-1-(triphenylmethyl)-1H-imidazol-4-yl]-2-propen-1-one A solution of potassium hydroxide (0.6 g) in methanol (5 ml) was added to a solution of 1-acetyl-4-methoxynaphthalene (0.6 g) and Intermediate 1 (1.0 g) in methanol (20 ml) at room temperature and the mixture was kept at 23° under nitrogen for 4 days. The resulting crystals were filtered off, washed with methanol and dried to give the *title compound* (1.1 g), m.p. 235°–237°.

Intermediate 27

(E)-3-[5-Methyl-1-(triphenylmethyl)-1H-imidazol-4-yl]-1-(2-methyl-1-naphthalenyl)-2-propen-1-one A mixture of 1-acetyl-2-methylnaphthalene (1.05 g), Intermediate 1 (2.0 g) and potassium hydroxide (0.5 g) in methanol (25 ml) was heated at 50° for 24 h, cooled on ice and filtered. The solid was washed with water (100 ml) and dried (75°, in vacuo, 2 h) to give the *title compound* (2.39 g), m.p. 222°–224°.

Intermediate 28

(E)-1-[(1,1'-Biphenyl)-3-yl]-3-[5-methyl-1-(triphenylmethyl)-1H-imidazol-4-yl]-2-propen-1-one A mixture of potassium hydroxide (0.6 g), 3-phenylacetophenone, (0.8 g) and Intermediate 1 (1.44 g) in methanol (25 ml) was kept at 23° for 4 days after which time an oil had separated. The supernatant solution was decanted off and the residual oil was purified by FCC eluting firstly with dichloromethane/hexane (4:1), and then with dichloromethane/ether (1:1) to give the *title compound* (0.9 g) as a foam.

Analysis Found: C,85.6; H,5.8; N,4.95; $C_{38}H_{30}N_2O$ requires C,86.0; H,5.7; N,5.3%.

Intermediate 29

(E)-1-(1-Methyl-1H-indazol-3-yl)-3-[5-methyl-1-(triphenylmethyl)-1H-imidazol-4-yl]-2-propen-1-one A mixture of 1-(1-methyl-1H-indazol-3-yl)ethanone (0.75 g), Intermediate 1 (1.5 g) and potassium hydroxide (0.375 g) in methanol (12.5 ml) was stirred at 60° for 5 h and then cooled. The solid was filtered off, washed successively with methanol (3×15 ml) and water (25 ml) and dried in vacuo to give the *title compound* (1.9 g), m.p. 223°–225°.

Intermediate 30

(E)-1-(2-Methoxy-1-naphthalenyl)-3-[5-methyl-1-(triphenylmethyl)-1H-imidazol-4-yl]-2-propen-1-one A mixture of 1-acetyl-2-methoxynaphthalene (1.14 g), Intermediate 1 (2.0 g) and potassium hydroxide (0.5 g) in methanol (25 ml) was stirred at 50° for 18 h, cooled and added to water (100 ml). The precipitate was collected, recrystallised from hot methanol (ca. 50 ml) and dried to give the *title compound* (2.59 g), m.p. 220°–222°.

Intermediate 31

(E)-3-(5-Methyl-1H-imidazol-4-yl)-1-(1H-pyrrolo-[2,3-b]-pyridin-3-yl)-2-propen-1-one A solution of 1-(1H-pyrrolo-[2,3-b]-pyridin-3-yl)ethanone (0.73 g) in dry THF (40 ml) at −50° under nitrogen was treated with lithium diisopropylamide (1.5M solution in cyclohexane; 7.6 ml) and stirred at 0° for 45 min. A solution of Intermediate 1 (2.4 g) in dry THF (20 ml) was added and the mixture was stirred for 5 min. It was then cooled to −50°, quenched with acetic acid (5 ml) and evaporated in vacuo. Acetic acid (90 ml) and p-toluenesulphonic acid monohydrate (5.0 g) were added and the mixture was heated under nitrogen at reflux for 2.5 h. It was then cooled and partitioned between 2N sodium hydroxide (700 ml) and dichloromethane (4×250 ml; discarded). The aqueous phase was acidified to pH 7 (with 2N hydrochloric acid) and extracted with chloroform/methanol (3:2) (4×250 ml). These organic extracts were dried, evaporated in vacuo and the residual solid was triturated with dichloromethane/ether (1:1) (100 ml), to give the *title compound* (0.78 g), t.l.c. (System A, 89:10:1) Rf 0.1.

Intermediate 32

2,3-Dihydro-3-(5-methyl-1H-imidazol-4-yl)-1H-naphtho[2,1-b]pyran-1-one

Lithium diisopropylamide (1.5M solution in cyclohexane; 7.9 ml) was added dropwise to a cold (−50°) stirred solution of 1-(2-hydroxy-1-naphthalenyl)ethanone (1.0 g) in dry THF (75 ml) under nitrogen. After 45 min., Intermediate 1 (2.0 g) was added and stirring was continued while warming to 0° over 1.25 h. Acetic acid (90 ml) was added to quench the reaction, followed by p-toluenesulphonic acid monohydrate (5.0 g) and the solution was heated under nitrogen at reflux for 24 h. The cooled solution was basified (to pH8) with 5N sodium hydroxide and extracted with dichloromethane (4×150 ml). The combined organic layers were washed with brine (3×100 ml), dried and evaporated in vacuo to give a solid. Trituration with methanol/water (9:1) (100 ml) followed by ether (3×50 ml) gave the *title compound* (930 mg), m.p. 214°–217° (decomp.).

Intermediate 33

1-(1-Methyl-1H-indol-4-yl)ethanone

Methyl lithium (1.59M solution in ether; 13.8 ml) was added dropwise to a stirred cold (−65° to −55°) solution of 1-methyl-1H-indole-4-carboxylic acid (1.75 g) in dry THF (50 ml) under nitrogen and stirring was continued while the mixture warmed to 0° over 2 h. The reaction was then quenched with saturated ammonium chloride solution (50 ml) and the layers were separated. The aqueous layer was further extracted with dichloromethane (2×50 ml) and the combined organic layers were washed with brine (2×50 ml), dried and evaporated in vacuo. The residual solid (1.8 g) was purified by FCC eluting with dichloromethane to give the *title compound* (1.6 g), m.p. 63°–64°.

GENERAL HYDROGENATION PROCEDURE

Examples 1 to 15 were all prepared by hydrogenation of a solution or suspension of the appropriate enone in methanol or ethanol at room temperature and atmospheric pressure over a stirred suspension of pre-reduced 10% palladium oxide on carbon catalyst in methanol or ethanol, until hydrogen uptake had ceased. The resulting suspension was filtered and the required product was obtained from the filtrate by one of a variety of conventional purification techniques, and maleate formation. Maleate formation (except where otherwise stated) consisted of dissolving the free base in ethanol (either at room temperature or at an elevated temperature), and adding to this solution a solution of maleic acid in ethanol. The resulting solution was either evaporated to dryness or diluted with dry ether to precipitate the title compound. Example 1 is described in full.

EXAMPLE 1

3-(5-Methyl-1H-imidazol-4-yl)-1-(2-naphthalenyl)-1-propanone maleate

A solution of (E)-3-(5-methyl-1H-imidazol-4-yl)-1-(2-naphthalenyl)-2-propen-1-one maleate (300 mg) in hot methanol (90 ml) was hydrogenated at room temperature and atmospheric pressure over a stirred suspension of pre-reduced 10% palladium oxide on carbon (50% aqueous paste; 30 mg) in methanol (10 ml) for 16 h. The suspension was filtered, evaporated in vacuo, and the residual oil (ca. 350 mg) was partitioned between dichloromethane (3×50 ml) and 2N sodium carbonate (50 ml). The combined organic extracts were dried and evaporated in vacuo. The residual oil (300 mg) was dissolved in absolute ethanol (6 ml) and treated with a solution of maleic acid (100 mg) in ethanol (1 ml). Dilution with dry ether (ca. 75 ml) afforded the *title compound* (210 mg) as a solid, m.p. 137°–138°, t.l.c. (System A, 89:10:1) Rf 0.33.

EXAMPLE 2

1-(5-Fluoro-1-naphthalenyl)-3-(5-methyl-1H-imidazol-4-yl)-1-propanone maleate The filtrate from the hydrogenation of 1-(5-fluoro-1-naphthalenyl)-3-(5-methyl-1H-imidazol-4-yl)-2-propen-1-one (1.01 g) was treated with maleic acid (418 mg) and the resultant solution was evaporated to dryness to give a solid. This was recrystallised from methanol/ethyl acetate to give the *title compound* (920 mg), m.p. 138°–140°.

Analysis Found: C,63.5; H,4.6; N,6.9; $C_{17}H_{15}FN_2O.C_4H_4O_4$ requires C,63.3; H,4.8; N,7.0%.

EXAMPLE 3

3-(5-Methyl-1H-imidazol-4-yl)-1-phenyl-1-propanone maleate

The filtrate from the hydrogenation of (E)-3-(5-methyl-1H-imidazol-4-yl)-1-phenyl-2-propen-1-one maleate (0.37 g) was concentrated in vacuo to ca. 5 ml and diluted with ether (200 ml) to precipitate a solid (290 mg). This was partitioned between dichloromethane (2×50 ml) and 2N sodium carbonate solution (50 ml; discarded) and the combined organic layers were dried and evaporated in vacuo. The resultant oil was purified by FCC eluting with System A (95:5:0.5) to give the free base of the title compound (132 mg) as a solid. Maleate formation gave the *title compound* (170 mg), m.p. 94°–95°.

Water Analysis Found: 0.8% w/w≡0.15 mol $H_2O$.
Analysis Found: C,61.1; H,5.4; N,8.2; $C_{13}H_{14}N_2O.C_4H_4O_4$. 0.15 $H_2O$ requires C,61.3; H,5.5; N,8.4%.

EXAMPLE 4

1-(2-Methoxyphenyl)-3-(5-methyl-1H-imidazol-4-yl)-1-propanone maleate

The filtrate from the hydrogenation of (E)-1-(2-methoxyphenyl)-3-(5-methyl-1H-imidazol-4-yl)-2-propen-1-one (0.75 g) was evaporated to leave a semi-solid (ca. 0.75 g) which was purified by SPCC eluting with System A (200:8:1) to give a gum (0.6 g). Maleate formation gave the *title compound* (0.69 g), m.p. 125°–128°.

Analysis Found: C,60.3; H,5.6; N,7.5; $C_{14}H_{16}N_2O_2.C_4H_4O_4$ requires C,60.0; H,5.6; N,7.8%.

EXAMPLE 5

3-(5-Methyl-1H-imidazol-4-yl)-1-(3,5-dimethylphenyl)-1-propanone maleate

The filtrate from the hydrogenation of (E)-3-(5-methyl-1H-imidazol-4-yl)-1-(3,5-dimethylphenyl)-2-propen-1-one (0.2 g) was evaporated to give an oil (0.2 g) which was dissolved in methanol (15 ml) containing maleic acid (0.1 g). The mixture was evaporated to give a solid which was triturated with ether, filtered and dried in vacuo to give the *title compound* (0.21 g), m.p. 151°–152°.

Analysis Found: C,63.7; H,6.2; N,7.9; $C_{15}H_{18}N_2O.C_4H_4O_4$ requires C,63.7; H,6.2; N,7.8%.

EXAMPLE 6

1-(2-Methyl-3-benzofuranyl)-3-(5-methyl-1H-imidazol-4-yl)-1-propanone, compound with maleic acid The filtrate from the hydrogenation of (E)-1-(2-methyl-3-benzofuranyl)-3-(5-methyl-1H-imidazol-4-yl)-2-propen-1-one (250 mg) was evaporated to give a solid (250 mg). The product of maleate formation was triturated with dry ether (3×30 ml) to give a solid (285 mg), a sample of which (245 mg) was recrystallised from hot methanol/ethyl acetate (1:3) to give the *title compound* (120 mg), m.p. 213°–215°, t.l.c. on triethylamine impregnated silica (ethyl acetate/methanol, 19:1) Rf 0.36.

N.m.r. indicates 0.32 mol of maleic acid present.

EXAMPLE 7

1-(2-Benzofuranyl)-3-(5-methyl-1H-imidazol-4-yl)-1-propanone maleate

The filtrate from the hydrogenation of (E)-1-(2-benzofuranyl)-3-(5-methyl-1H-imidazol-4-yl)-2-propen-1-one (500 mg) was evaporated and the resulting oil was purified by FCC eluting with System A (100:10:1) to give the free base of the title compound (210 mg) as a foam. The product of maleate formation was recrystallised from ethanol (8 ml) to give the *title compound* (160 mg), m.p. 152°–154°.

Analysis Found: C,61.3; H,4.9; N,7.4; $C_{15}H_{14}N_2O_2.C_4H_4O_4$ requires C,61.6; H,4.9; N,7.6%.

EXAMPLE 8

1-(2-Methylbenzo[b]thien-3-yl)-3-(5-methyl-1H-imidazol-4-yl)-1-propanone maleate The filtrate from the hydrogenation of (E)-1-(2-methylbenzo[b]-thien-3-yl)-3-(5-methyl-1H-imidazol-4-yl)-2-propen-1-one (195 mg) was evaporated to give an oil (160 mg). The product of maleate formation was triturated with dry ether (3×10 ml) to give the *title compound* (165 mg), m.p. 131°–132°.

Analysis Found: C,60.1; H,5.0; N,6.9; $C_{16}H_{16}N_2OS.C_4H_4O_4$ requires C,60.0; H,5.0; N,7.0%.

EXAMPLE 9

1-(Benzo[b]thien-2-yl)-3-(5-methyl-1H-imidazol-4-yl)-1-propanone, compound with maleic acid The filtrate from the hydrogenation of (E)-1-[benzo[b]thien-2-yl]-3-(5-methyl-1H-imidazol-4-yl)-2-propen-1-one (667 mg) was treated with maleic acid (145 mg). The resultant solution was evaporated to give a solid which was heated to reflux in ethyl acetate (150 ml) and the suspension was then cooled to room temperature. The organic solution was decanted and the remaining solid was dried in vacuo to give the *title compound* (371 mg), m.p. 141°–143°.

N.m.r. indicates 0.8 mol of maleic acid present.
Water Analysis Found: 1.5% w/w≡0.27 mol $H_2O$.
Analysis Found: Found: C,59.0; H,4.8; N,7.2; $C_{15}H_{14}N_2OS.0.8C_4H_4O_4$ 0.27 $H_2O$ requires C,59.4; H,4.9; N,7.6%.

EXAMPLE 10

1-(3-Benzofuranyl)-3-(5-methyl-1H-imidazol-4-yl)-1-propanone maleate

The filtrate from the hydrogenation of (E)-1-(3-benzofuranyl)-3-(5-methyl-1H-imidazol-4-yl)-2-propen-1-one (200 mg) was evaporated to give an oil (169 mg). The solid product of maleate formation was recrystallised from ethanol (4 ml) to give the *title compound* (118 mg), m.p. 139°–140°.
Analysis Found: C,61.6; H,4.9; N,7.6; $C_{15}H_{14}N_2O_2.C_4H_4O_4$ requires C,61.6; H,4.9; N,7.6%.

EXAMPLE 11

3-(5-Methyl-1H-imidazol-4-yl)-1-(1-methyl-1H-indol-2-yl)-1-propanone maleate

The filtrate from the hydrogenation of (E)-3-(5-methyl-1H-imidazol-4-yl)-1-(1-methyl-1H-indol-2-yl)-2-propen-1-one (295 mg) was evaporated to give a solid (250 mg). Maleate formation gave a solid (194 mg), a portion of which (180 mg) was treated with 8% aqueous sodium bicarbonate (20 ml) and extracted with ethyl acetate. The organic extract was dried and evaporated to give an oil which was purified by FCC eluting with System A (100:10:1) to give the free base of the title compound as an oil. Maleate formation gave the *title compound* (160 mg), m.p. 137°–139°.
Analysis Found: C,62.4; H,5.5; N,10.8; $C_{16}H_{17}N_3O.C_4H_4O_4$ requires C,62.7; H,5.5; N,11.0%.

EXAMPLE 12

3-(5-Methyl-1H-imidazol-4-yl)-1-(1H-pyrrolo-[2,3-b]-pyridin-3-yl)-1-propanone maleate A solution of (E)-3-(5-methyl-1H-imidazol-4-yl)-1-(1H-pyrrolo-[2,3-b]-pyridin-3-yl)-2-propen-1-one (300 mg) in dichloromethane/methanol (1:1) (100 ml) was hydrogenated as described in the General Procedure. The resulting filtrate was evaporated in vacuo to give a foam (0.30 g). Maleate formation gave a solid (235 mg), a portion of which (210 mg) was partitioned between chloroform/methanol (5:1) (3×50 ml) and 2N sodium carbonate (50 ml) and the combined, dried organic layers were evaporated in vacuo to give a solid (155 mg). Maleate formation gave the *title compound* (210 mg), m.p. 185°–190°.
Analysis Found: C,58.4; H,5.0; N,15.0; $C_{14}H_{14}N_4O.C_4H_4O_4$ requires C,58.4; H,5.0; N,15.1%.

EXAMPLE 13

3-(5-Methyl-1H-imidazol-4-yl)-1-(1,2,4-trimethyl-1H-pyrrol-3-yl)-1-propanone maleate The filtrate from the hydrogenation of (E)-3-(5-methyl-1H-imidazol-4-yl)-1-(1,2,4-trimethyl-1H-pyrrol-3-yl)-2-propen-1-one (520 mg) was evaporated to give the free base of the title compound as an oil (480 mg). The product of maleate formation was crystallised from ethyl acetate (80 ml) to give the *title compound* (516 mg), m.p. 106°–108°.
Water Analysis Found: 1.87% w/w≡0.38 mol $H_2O$.
Analysis Found: C,58.6; H,6.3; N,11.2; $C_{14}H_{19}N_3O.C_4H_4O_4.0.38$ $H_2O$ requires C,58.7; H,6.5; N,11.4%.

EXAMPLE 14

1-(2,5-Dimethyl-3-furanyl)-3-(5-methyl-1H-imidazol-4-yl)-1-propanone maleate

The filtrate from the hydrogenation of (E)-1-(2,5-dimethyl-3-furan-yl)-3-(5-methyl-1H-imidazol-4-yl)-2-propen-1-one (485 mg) was evaporated to give the free base of the title compounds as an oil (460 mg). The product of maleate formation was crystallised from ethanol (15 ml) to give the *title compound* (303 mg), 130°–131°.
Analysis Found: C,59.0; H,5.9; N,8.0; $C_{13}H_{16}N_2O_2.C_4H_4O_4$ requires C,58.6; H,5.8; N,8.0%.

EXAMPLE 15

1-(2,5-Dimethyl-3-thienyl)-3-(5-methyl-1H-imidazol-4-yl)-1-propanone maleate

The filtrate from the hydrogenation of (E)-1-(2,5-dimethyl-3-thienyl)-3-(5-methyl-1H-imidazol-4-yl)-2-propen-1-one hemi-succinate (200 mg) was evaporated to give a gum (0.25 g) which was adsorbed onto silica (ca. 1 g) and purified by FCC eluting with System A (75:8:1) to give the free base of the title compound (0.15 g). Maleate formation gave the *title compound* (0.175 g), m.p. 126°–128°.
Analysis Found: C,56.2; H,5.6; N,7.5; $C_{13}H_{16}N_2OS.C_4H_4O_4$ requires C,56.0; H,5.5; N,7.7%.

EXAMPLE 16

3-(5-Methyl-1H-imidazol-4-yl)-1-(1-naphthalenyl)-1-propanone succinate

A suspension of (E)-3-(5-methyl-1H-imidazol-4-yl)-1-(1-naphthalenyl)-2-propen-1-one maleate (0.38 g) in methanol (50 ml) was hydrogenated at room temperature and atmospheric pressure over a stirred suspension of pre-reduced 10% palladium oxide on carbon (50% aqueous paste; 40 mg) in methanol (10 ml) for 2 h. The reaction mixture was filtered, the filtrate was concentrated in vacuo to ca. 5 ml, and diluted with dry ether (ca. 150 ml) to precipitate the *title compound* (0.28 g) as a solid, m.p. 107°–108°.
Analysis Found: C,65.9; H,5.8; N,7.1; $C_{17}H_{16}N_2O.C_4H_6O_4$ requires C,66.0; H,5.8; N,7.3%.

EXAMPLE 17

1-(4-Methoxy-1-naphthalenyl)-3-(5-methyl-1H-imidazol-4-yl)-1-propanone maleate

A solution of (E)-1-(4-methoxy-1-naphthalenyl)-3-[5-methyl-1-(triphenylmethyl)-1H-imidazol-4-yl]-2-propen-1-one (0.9 g) in a mixture of THF (15 ml), water (3 ml) and acetic acid (2 ml) was heated on a steam bath for 30 min. The mixture was then concentrated to remove most of the THF and the residue was diluted with 0.5M hydrochloric acid (10 ml). The mixture was washed with ether (2×25 ml; discarded), basified with solid potassium carbonate and extracted with dichloromethane (2×25 ml). The organic phase was dried and evaporated to give a solid (0.4 g) which was dissolved in ethanol (25 ml) and hydrogenated at room temperature and atmospheric pressure over a stirred suspension of pre-reduced 10% palladium oxide on carbon (50% aqueous paste; 0.1 g) in ethanol for 1 h. The mixture was filtered and maleic acid (0.15 g) was dissolved in the filtrate. The filtrate was then evaporated in vacuo to give a solid which was triturated with ether (50 ml) and filtered to give the *title compound* (0.35 g), m.p. 150°–151°.

Analysis Found: C,64.25; H,5.5; N,6.7; $C_{18}H_{18}N_2O_2 \cdot C_4H_4O_4$ requires C,64.4; H,5.4; N,6.8%.

EXAMPLE 18

3-(5-Methyl-1H-imidazol-4-yl)-1-(2-methyl-1-naphthalenyl)-1-propanone maleate

A mixture of (E)-3-[5-methyl-1-(triphenylmethyl)-1H-imidazol-4-yl]-1-(2-methyl-1-naphthalenyl)-2-propen-1-one (1.25 g), acetic acid (10 ml), THF (10 ml) and water (10 ml) was heated on a steam bath for 1 h. The mixture was then hydrogenated according to the General Procedure and the resulting filtrate was evaporated in vacuo and partitioned between dichloromethane (3×75 ml) and 0.2N sodium hydroxide (100 ml). The combined organic layers were dried and evaporated in vacuo to leave a foam (1.3 g) which was purified by FCC eluting with System A (94.5:5:0.5) to give the free base of the title compound as an oil. The product of maleic acid formation was triturated with ether to give the *title compound* (0.78 g), m.p. 108°–109°.

Analysis Found: C,66.7; H,5.5; N,6.9; $C_{18}H_{18}N_2O \cdot C_4H_4O_4$ requires C,67.0; H,5.6; N,7.1%.

EXAMPLE 19

1-[(1,1'-Biphenyl)-3-yl]-3-(5-methyl-1H-imidazol-4-yl)-1-propanone maleate

A solution of (E)-1-[(1,1'-biphenyl)-3-yl]-3-[5-methyl-1-(triphenylmethyl)-1H-imidazol-4-yl]-2-propen-1-one (0.7 g) in a mixture of THF (15 ml), water (5 ml) and acetic acid (3 ml) was heated on a steam bath for 1 h. The mixture was basified with 2N sodium carbonate and extracted with dichloromethane (2×30 ml). The combined, dried organic extracts were evaporated to give an oil which was purified by FCC eluting with ethyl acetate/triethylamine (100:1) and then with ethyl acetate/methanol (5:1) to give a foam (0.26 g) which was hydrogenated according to the General Procedure. Maleic acid (0.1 g) was dissolved in the resulting filtrate and the solution was evaporated to give a gum which was triturated with ether to give the *title compound* (0.26 g) as a solid, m.p. 122°–123°.

Analysis Found: C,68.2; H,5.6; N,7.0; $C_{19}H_{18}N_2O \cdot C_4H_4O_4$ requires C,68.0; H,5.5; N,6.9%.

EXAMPLE 20

3-(5-Methyl-1H-imidazol-4-yl)-1-(1-methyl-1H-indazol-3-yl)-1-propanone maleate

A mixture of (E)-1-(1-methyl-1H-indazol-3-yl)-3-[5-methyl-1-(triphenylmethyl)-1H-imidazol-4-yl]-2-propen-1-one (1.3 g) in water (10 ml), acetic acid (10 ml) and THF (10 ml) was heated at reflux for 1 h, and then cooled. It was then mixed with ethanol (70 ml) and hydrogenated at room temperature and atmospheric pressure over a stirred suspension of pre-reduced 10% palladium oxide on carbon (130 mg) in ethanol for 1 h. The mixture was filtered, evaporated in vacuo and the residual semi-solid was purified by FCC eluting with System A (89:10:1) to give the free base of the title compound as a solid (0.62 g). This was dissolved in ethanol (15 ml) and treated with a solution of maleic acid (275 mg) in methanol (1 ml). Concentration in vacuo to 2 ml followed by dilution with ethyl acetate (50 ml) afforded the *title compound* (0.75 g), m.p. 153°–154°.

Analysis Found: C,59.4; H,5.3; N,14.3; $C_{15}H_{16}N_4O \cdot C_4H_4O_4$ requires C,59.4; H,5.2; N,14.6%.

EXAMPLE 21

1-(2-Methoxy-1-naphthalenyl)-3-(5-methyl-1H-imidazol-4-yl)-1-propanone, compound with hydrogen chloride and acetic acid (E)-1-(2-Methoxy-1-naphthalenyl)-3-[5-methyl-1-(triphenylmethyl)-1H-imidazol-4-yl]-2-propen-1-one (1.0 g) was hydrogenated according to the General Procedure and the resulting filtrate was evaporated in vacuo. A mixture of water (10 ml), acetic acid (10 ml) and THF (10 ml) was added and the mixture was heated on a steam bath for 1.5 h. The solution was cooled and partitioned between 0.2N hydrochloric acid (150 ml) and dichloromethane (150 ml; discarded). The aqueous phase was basified with 2N sodium hydroxide (to pH 7) and extracted with dichloromethane (3×150 ml). The combined, dried organic layers were evaporated in vacuo and the residual oil was triturated with dry ether (75 ml) to give the *title compound* (0.47 g) as a solid, m.p. 153°–158°, t.l.c. (System A, 89:10:1) Rf 0.44.

N.m.r. indicates 0.33 mol acetic acid present.

Analysis Found: C,66.2; H,6.1; N,8.1; Cl,6.8; $C_{18}H_{18}N_2O_2 \cdot 0.33 C_2H_4O_2 \cdot 0.66 HCl$ requires C,66.2; H,5.95; N,8.3; Cl,6.9%.

EXAMPLE 22

3-(5-Methyl-1H-imidazol-4-yl)-1-(4-quinolinyl)-1-propanone maleate

A solution of 3-(5-methyl-1H-imidazol-4-yl)-1-(quinolin-4-yl)-2-propen-1-one (0.4 g) and tris(triphenylphosphine)rhodium (I) chloride (0.08 g) in toluene (90 ml) and ethanol (60 ml) was stirred under hydrogen for 4 h. A further batch of tris(triphenylphosphine)rhodium (I) chloride (0.02 g) was added and the solution was stirred under hydrogen at 20° for 1 h and then at 50° for 1 h. The solution was then evaporated in vacuo to give a gum (ca. 0.6 g) which was purified by FCC eluting with System A (89:10:1) to give a gum (0.083 g) which was dissolved in absolute ethanol (1 ml) and treated with a solution of maleic acid (36 mg) in ethanol (1 ml). The resulting solution was diluted with ether (ca. 50 ml) to precipitate the *title compound* (87 mg) as a solid, m.p. 110°–112°, t.l.c. (System A, 89:10:1) Rf 0.25.

EXAMPLE 23

1-(2-Hydroxy-1-naphthalenyl)-3-(5-methyl-1H-imidazol-4-yl)-1-propanone maleate

A suspension of 2,3-dihydro-3-(5-methyl-1H-imidazol-4-yl)-1H-naphtho[2,1-b]pyran-1-one (400 mg) in ethanol (60 ml) was added to a stirred suspension of 10% palladium on carbon (45 mg) in ethanol (15 ml) under hydrogen. After 2 h, a solution of potassium hydroxide (100 mg) in methanol (2.5 ml) was added. Stirring was continued for 5 h and the reaction was then neutralised with saturated ammonium chloride solution (5 ml), filtered and evaporated in vacuo. The residual oil was dissolved in ethanol (5 ml) and treated with a solution of maleic acid (167 mg) in ethanol (2 ml). Dilution with ether (100 ml) afforded a gum which, on trituration with hot ethyl acetate, gave a solid which was recrystallised from ethanol/ethyl acetate (1:5) (70 ml) to give a solid (0.3 g). The mother liquors were evaporated in vacuo, combined with this solid, and partitioned between dichloromethane (3×50 ml) and 2N sodium carbonate solution (50 ml). The combined, dried organic layers were evaporated and purified by FCC eluting with System A (95:5:0.5), to give the free base of the title compound as a foam (315 mg). This was dissolved in ethanol (5 ml), treated with a solution of maleic acid (125 mg) in ethanol (1 ml) and diluted with dry ether (75 ml) to give the *title compound* (315 mg) as a solid, m.p. 155°–157°.

Analysis Found: C,63.4; H,5.0; N,6.9; $C_{17}H_{16}N_2O_2 \cdot C_4H_4O_4$ requires C,63.6; H,5.1; N,7.1%.

EXAMPLE 24

1-(Benzo[b]thien-3-yl)-3-(5-methyl-1H-imidazol-4-yl)-1-propanone maleate

A solution of potassium hydroxide (1.0 g) in methanol (10 ml) was added to a solution of 3-acetylbenzo[b]thiophene (2.0 g) and Intermediate 1 (4.0 g) in methanol (40 ml) under nitrogen. The mixture was stirred at reflux for 4 h then at room temperature for 65 h. The suspension was filtered and the solid obtained was heated at reflux in a mixture of acetic acid (20 ml), water (20 ml) and THF (20 ml) for 1.5 h. The solution was allowed to cool to room temperature and was then hydrogenated at room temperature and atmospheric pressure over a stirred suspension of pre-reduced 10% palladium oxide on carbon (50% aqueous paste, 2.0 g) in ethanol (50 ml) for 18 h. The mixture was filtered, evaporated and the residue was treated with saturated potassium carbonate solution (100 ml) and extracted with dichloromethane (3×50 ml). The combined organic extracts were dried and evaporated to give an oil (ca. 5.5 g) which was purified by FCC eluting with System A (150:10:1) to give a foam (1.52 g). This material was dissolved in dichloromethane (20 ml) and treated with a solution of maleic acid (686 mg) in ethanol (5 ml). The solvent was removed in vacuo and the residue was triturated with dry ether (5×30 ml) to give the *title compound* as a solid (1.87 g), m.p. 164°–165°. The sample was dried in vacuo at 100° for 24 h and was then dissolved in hot ethanol (100 ml). The resultant solution was filtered and the filtrate was evaporated to leave a solid. Dry ether (150 ml) was added and the suspension was filtered. The solid obtained was washed with dry ether (3×50 ml) and dried in vacuo at 75° for 36 h to give the *title compound* (1.77 g) as a solid, m.p. 164°–165°.

N.m.r. indicates 0.55% w/w ethanol present≡0.046 mol.

Water Analysis Found 0.87% w/w≡0.19 mol $H_2O$.

Analysis Found: C,58.9; H,4.7; N,7.1; $C_{15}H_{14}N_2OS \cdot C_4H_4O_4 \cdot 0.19H_2O \cdot 0.046C_2H_5OH$ requires C,58.5; H,4.8; N,7.2%.

EXAMPLE 25

1-(6-Fluoro-1-naphthalenyl)-3-(5-methyl-1H-imidazol-4-yl)-1-propanone maleate

A suspension of 1-(6-fluoro-1-naphthalenyl)ethanone (404 mg) and Intermediate 1 (760 mg) in methanol (10 ml) was treated with a solution of potassium hydroxide (180 mg) in methanol (2 ml). The mixture was heated at reflux for 4 h, allowed to stand at room temperature for 18 h and then concentrated in vacuo to ca. 2 ml. Acetic acid (8 ml), water (5 ml) and THF (15 ml) were added and the solution was heated at reflux for 3 h. The reaction mixture was added cautiously to 8% aqueous sodium bicarbonate solution (150 ml) and the mixture was extracted with dichloromethane (3×40 ml). The combined, dried organic extracts were evaporated to give an oil which was hydrogenated according to the General Procedure and the resulting filtrate was evaporated to give an oil. This oil was purified by FCC eluting with System A (100:3:0.3) and then with System A (100:10:1) to give a solid (374 mg) which was dissolved in ethanol (20 ml) and treated with a solution of maleic acid (154 mg) in ethanol (20 ml). The mixture was evaporated to give a solid which was stirred under dry ether (100 ml) for 1 h to give a fine suspension. The ether was decanted and the remaining solid was dried in vacuo to give the *title compound* (487 mg), m.p. 145°–148°.

Analysis Found: C,63.3; H,4.8; N,6.9; $C_{17}H_{15}N_2O \cdot C_4H_4O_4$ requires C,63.3; H,4.8; N,7.0%.

EXAMPLE 26

3-(5-Methyl-1H-imidazol-4-yl)-1-(1-methyl-1H-indol-4-yl)-1-propanone maleate

A mixture of 1-(1-methyl-1H-indol-4-yl)ethanone (0.75 g), Intermediate 1 (1.5 g) and potassium hydroxide (0.375 g) in methanol (12.5 ml) was stirred at 50° for 24 h. The cooled mixture was partitioned between dichloromethane (3×75 ml) and brine (75 ml) and the combined, dried organic extracts were evaporated in vacuo. The residual foam (2.3 g) was heated at reflux in a mixture of water (10 ml), acetic acid (10 ml) and THF (10 ml) for 2 h. The cooled solution was hydrogenated at room temperature and atmospheric pressure over a stirred suspension of pre-reduced 10% palladium oxide on carbon (50% aqueous paste; 200 mg) in ethanol for 1 h. The suspension was filtered, evaporated in vacuo, and the residue (7 g) was purified by FCC eluting with System A (89:10:1) to give the free base of the title compound as a foam (1.03 g). This was dissolved in ethanol (10 ml) and treated with a solution of maleic acid (447 mg) in methanol (1 ml). Dilution with dry ether (100 ml) afforded the *title compound* (1.18 g), m.p. 130°–131°.

Analysis Found: C,62.3; H,5.5; N,10.8; $C_{16}H_{17}N_3O \cdot C_4H_4O_4$ requires C,62.65; H,5.5; N,11.0%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

CAPSULES

|  | mg/capsule |
|---|---|
| Active Ingredient | 0.5 |
| *Starch 1500 | 98.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

Direct Compression Tablet

|  | mg/tablet | |
|---|---|---|
| Active Ingredient | 0.50 | 10.00 |
| Calcium Hydrogen Phosphate BP* | 87.25 | 77.75 |
| Croscarmellose Sodium NF | 1.80 | 1.80 |
| Magnesium Stearate BP | 0.45 | 0.45 |
| Compression weight | 90.00 | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

SYRUP

This may be either a sucrose or sucrose free presentation.

| Sucrose-Free Syrup | mg/5 ml dose |
|---|---|
| Active Ingredient | 0.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

|  | mg/ml | |
|---|---|---|
| Active ingredient | 0.05 | 1.0 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A compound of formula (I):

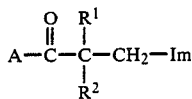

or a physiologically acceptable salt or solvate thereof, wherein $R^1$ and $R^2$, which may be the same or different, each represents a hydrogen atom or a $C_{1-6}$ alkyl group;

Im represents an imidazolyl group of formula:

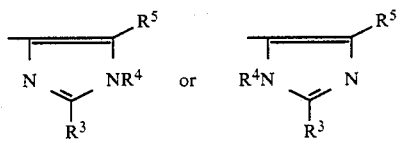

wherein one of the groups represented by $R^3$, $R^4$ and $R^5$ is a hydrogen atom or a $C_{1-6}$ alkyl, $C_{3-7}$ cycloalkyl, $C_{3-6}$ alkenyl, phenyl or phenyl $C_{1-3}$ alkyl group, and each of the other two groups, which may be the same or different, represents a hydrogen atom or a $C_{1-6}$ alkyl group; and A is a group

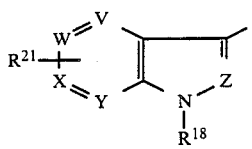

$R^{18}$ represents a hydrogen atom or a group $C_{1-6}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl, phenyl $C_{1-3}$ alkyl, $-CO_2R^{19}$, $-COR^{19}$, $-CONR^{19}R^{20}$ or $-SO_2R^{19}$ (wherein $R^{19}$ and $R^{20}$, which may be the same or different, each represents a hydrogen atom, a $C_{1-6}$ alkyl or $C_{3-7}$ cycloalkyl group, or a phenyl phenyl $C_{1-4}$ alkyl group, in which the phenyl group is optionally substituted by one or more $C_{1-4}$ alkyl, $C_{1-4}$ alkoxy or hydroxy groups or halogen atoms, with the proviso that $R^{19}$ does not represent a hydrogen atom when $R^{18}$ represents a group $-CO_2R^{19}$ or $-SO_2R^{19}$);

$R^{21}$ represents a hydrogen atom or a halogen atom or a hydroxy, $C_{1-4}$ alkoxy, phenyl $C_{1-3}$ alkoxy or $C_{1-6}$ alkyl group or a group $-NR^{22}R^{23}$ or $-CONR^{22}R^{23}$, (wherein $R^{22}$ and $R^{23}$, which may be the same or different, each represents a hydrogen atom or a $C_{1-4}$ alkyl or $C_{3-4}$ alkenyl group, or together with the nitrogen atom to which they are attached form a saturated 5 to 7 membered ring);

V, W, X and Y each independently represent a nitrogen atom or the group —CH—, and Z represents a nitrogen atom or the group —CR$^{24}$ (wherein R$^{24}$ represents a hydrogen atom or a C$_{1-6}$ alkyl, C$_{3-6}$ alkenyl, C$_{3-7}$ cycloalkyl, phenyl or phenyl C$_{1-3}$ alkyl group), with the proviso that one and only one of V, W, X, Y and Z represents a nitrogen atom.

2. A compound according to claim 1 in which R$^1$ and R$^2$ each represent a hydrogen atom.

3. A compound according to claim 1 in which R$^3$, R$^4$ and R$^5$ each independently represent a hydrogen atom or a C$_{1-4}$ alkyl group.

4. A compound according to claim 1 in which R$^3$ and R$^4$ each represent a hydrogen atom and R$^5$ is a C$_{1-6}$ alkyl, C$_{3-7}$ cycloalkyl, C$_{3-6}$ alkenyl, phenyl or phenyl C$_{1-3}$ alkyl group.

5. A compound according to claim 1 in which one of Y and Z represents a nitrogen atom, R$^{18}$ represents a hydrogen atom or a C$_{1-6}$ alkyl group, R$^{21}$ represents a hydrogen atom, and when Y is a nitrogen atom, R$^{24}$ is a hydrogen atom.

6. 3-(5-Methyl-1H-imidazol-4-yl)-1-(1-methyl-1H-indazol-3-yl)-1-propanone; and physiologically acceptable salts and solvates thereof.

7. A pharmaceutical composition for treating a condition caused by disturbance of "neuronal" 5HT function which comprises an effective amount to relieve said condition of a compound of formula (I) as defined in claim 1 or a physiologically acceptable salt or solvate thereof together with at least one physiologically acceptable carrier or diluent.

8. A method of treating a condition caused by disturbance of "neuronal" 5HT function which comprises administering to a patient an effective amount of a compound of formula (I) as defined in claim 1 or a physiologically acceptable salt or solvate thereof to relieve said condition.

* * * * *